(12) United States Patent
Abe et al.

(10) Patent No.: US 8,426,127 B2
(45) Date of Patent: Apr. 23, 2013

(54) FLUORESCENCE-PRODUCING MOLECULE

(75) Inventors: Hiroshi Abe, Saitama (JP); Yoshihiro Ito, Tokyo (JP); Jin Wang, Normam, OK (US); Kazuhiro Furukawa, Tokyo (JP)

(73) Assignee: Riken, Saitama (JP)

( * ) Notice: Subject to any disclaimer, the term of this patent is extended or adjusted under 35 U.S.C. 154(b) by 427 days.

(21) Appl. No.: 12/520,115

(22) PCT Filed: Dec. 19, 2007

(86) PCT No.: PCT/JP2007/074424
§ 371 (c)(1),
(2), (4) Date: Sep. 28, 2009

(87) PCT Pub. No.: WO2008/075718
PCT Pub. Date: Jun. 26, 2008

(65) Prior Publication Data
US 2010/0190159 A1    Jul. 29, 2010

(30) Foreign Application Priority Data

Dec. 19, 2006 (JP) ................. 2006-341245
Sep. 14, 2007 (JP) ................. 2007-239235

(51) Int. Cl.
*C12Q 1/68* (2006.01)
*C07D 307/77* (2006.01)

(52) U.S. Cl.
USPC .......................... 435/6.1; 549/265

(58) Field of Classification Search ........... 435/6.1; 549/235
See application file for complete search history.

(56) References Cited

U.S. PATENT DOCUMENTS

| | | | |
|---|---|---|---|
| 6,696,241 B2 | 2/2004 | Thompson et al. | |
| 2003/0055243 A1 | 3/2003 | Lee et al. | |
| 2006/0105410 A1 | 5/2006 | Maeda et al. | |
| 2007/0154899 A1* | 7/2007 | Coull et al. | 435/6 |

FOREIGN PATENT DOCUMENTS

| | | |
|---|---|---|
| JP | 2002-034595 | 2/2002 |
| JP | 2004-532805 | 10/2004 |
| JP | 2005-047898 | 2/2005 |
| WO | 00/03033 | 1/2000 |
| WO | 02/36832 | 5/2002 |
| WO | 2006/128138 | 11/2006 |

OTHER PUBLICATIONS

Novikova et al. Russian Journal of Organic Chemistry 34(12), 1762-1767, 1998.*
Handlon et al. Pharmaceutical Research, 1988, 5(5), 297-299.*
Novikova, E. et al., "Polymerization of Methyl Methacrylate Photoinitiated by Azidoxanthones and Azidofluoranes," Polimery, vol. 46, No. 6, Jan. 1, 2001, pp. 406-413.
Cai, J. et al., "Nucleic Acid-Triggered Fluorescent Probe Activation by the Staudinger Reaction," Journal of the American Chemical Society, vol. 126, No. 50, Nov. 23, 2004, pp. 16324-16325.
Lemieux, G. A. et al., "A Fluorogenic Dye Activated by the Staudinger Ligation," Journal of the American Chemical Society, vol. 125, No. 16, Mar. 28, 2003, pp. 4708-4709.
Abe Hiroshi et al., "A Reduction-Triggered Fluorescence Probe for Sensing Nucleic Acids," Bioconjugate Chemistry, vol. 19, No. 6, Jun. 2008, pp. 1219-1226.
Extended European Search Report for EP Application No. 07850894.2, mailed Mar. 22, 2010.
Adams et al., "A new caged $Ca^{2+}$, azid-1, is far more photosensitive than nitrobenzyl-based chelators" Chemistry and Biology, Current Biology, London, GB, vol. 4, No. 11, pp. 867-878, 1997.
European Office Action issued with respect to EP App. No. 07850894.2, dated Jan. 24, 2011.
Novikova, E. A. et al., "Synthesis and Structure of Some Azidofluoran Derivatives", Russian Journal of Organic Chemistry, 1998, vol. 34, No. 12, pp. 1762-1767.
International Preliminary Report on Patentability for International Application No. PCT/JP2007/074424, 2010.
International Search Report for International Application No. PCT/JP2007/074424, Mar. 22, 2010.

* cited by examiner

*Primary Examiner* — Nizal Chandrakumar
(74) *Attorney, Agent, or Firm* — Greenblum & Bernstein, P.L.C.

(57) ABSTRACT

It is an object of the present invention to provide an on-off type fluorescent compound used in gene analyses, which is highly stable and highly sensitive, and which enables amplification of a trace amount of gene signal and observation thereof. The present invention provides a compound represented by the following formula (1) or (2):

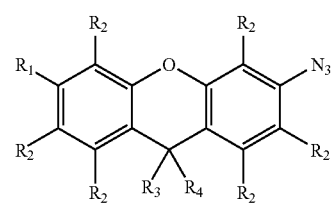

(1)

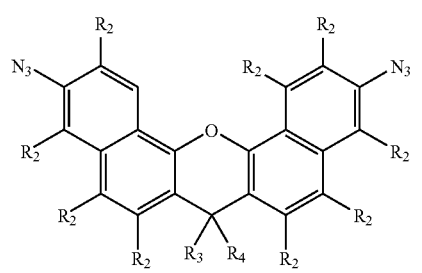

(2)

wherein $R_1$ represents an alkyl group containing 1 to 6 carbon atoms, an amino group, an amide group optionally having a protecting group or a substituent, a halogen atom, or a hydrogen atom; $R_2$ independently represents an alkyl group containing 1 to 6 carbon atoms, a halogen atom, or a hydrogen atom; $R_3$ represents an alkyl group containing 1 to 6 carbon atoms, an aryl group, or a hydrogen atom; $R_4$ represents a group containing an oxygen atom, or a hydrogen atom, wherein $R_3$ may bind to $R_4$ to form a ring.

3 Claims, 8 Drawing Sheets

Fig. 1

(A) fluorescence-producing molecule system nonfluorescent molecule → fluorescent molecule (B) Example of rhodamine derivative nonfluorescent molecule → fluorescent molecule

Fluorescent spectrum before and after light irradiation

Measurement condition

[jw]= 1 μM  excitation wavelength : 490nm

Excitation bandwidth: 3nm  Initiation wavelength: 400nm

Fluorescent bandwith: 5nm  Termination wavelength: 700 nm

Response: 0.5 sec  Data intake interval: 1nm

Sensitivity : Medium  Light irradiation time: 60sec

Fig. 9

```
5'-GCCGGCGG(Az)      (Red)TGTGGGCA-3'
3'-CGCGGCCGCC----------------ACACCCGTTC-5'   Ras-C (match)
3'-CGCGGCCGCC----------------ACAACCGTTC-5'   Ras-A (mismatch)
3'-CGCGGCCGCC----------------ACACCCGUUC-5'   Ras-C (RNA)(match)
```

FLUORESCENCE-PRODUCING MOLECULE

TECHNICAL FIELD

The present invention relates to a fluorescence-producing molecule which is useful as a labeling reagent for detecting biologically-relevant substances such as nucleic acids. More specifically, the present invention relates to a nonfluorescent molecule having an azido group, which is characterized in that it produces fluorescence when the azido group is reduced to an amino group. Furthermore, the present invention also relates to a labeling reagent comprising the aforementioned fluorescence-producing molecule and a method for detecting a target nucleic acid sequence using the aforementioned fluorescence-producing molecule.

BACKGROUND ART

As a method for detecting a nucleic acid molecule having a specific target nucleic acid sequence, a hybridization method using a probe having a nucleotide sequence complementary to the target nucleic acid sequence has been widely used. In the hybridization method, a probe having a nucleotide sequence complementary to the target nucleic acid sequence is prepared, and only a sample having a nucleotide sequence complementary to the nucleotide sequence of the probe is hybridized thereto with high selectivity. As a means for detecting a hybrid formed as a result of the hybridization, a method of labeling a probe nucleic acid with a radioisotope, a method of labeling a probe nucleic acid with a fluorescent substance, a method using a chemiluminescent reagent, and the like are applied. Fluorescent substances which can be used in the labeling of a nucleic acid include fluorescein, tetramethylrhodamine, Cy3, Cy5, and the like. A fluorescent nucleic acid probe labeled with such fluorescent substance has a high background fluorescence signal. Thus, it has been difficult to carry out highly sensitive measurement using such probe.

DISCLOSURE OF THE INVENTION

Object to be Solved by the Invention

It is an object of the present invention to solve the aforementioned problems of prior art techniques. That is to say, it is an object of the present invention to provide an on-off type fluorescent compound (a fluorescence-producing molecule system) used in gene analyses, which is highly stable (namely, being active for a long period of time) and highly sensitive, and which enables amplification of a trace amount of gene signal and observation thereof. In addition, it is another object of the present invention to provide a labeling reagent for detecting a biologically-relevant substance using the aforementioned on-off type fluorescent compound.

Means for Solving the Object

As a result of intensive studies directed towards achieving the aforementioned objects, the present inventors have succeeded in synthesizing a nonfluorescent molecule having a fluorescent substance skeleton such as a rhodamine skeleton and having an azido group in the molecule, which is characterized in that the molecule produces fluorescence when the azido group is reduced to an amino group. Moreover, the inventors have found that a first nucleic acid probe labeled with the aforementioned nonfluorescent molecule and a second nucleic acid probe labeled with a molecule having reduction action are hybridized to a target nucleic acid sequence, so as to reduce the azido group of the nonfluorescent molecule in the first nucleic acid probe to an amino group, and that a target nucleic acid sequence can be detected by detecting the thus produced fluorescence. The present invention has been completed based on these findings.

The present invention provides a compound represented by the following formula (1) or (2):

wherein $R_1$ represents an alkyl group containing 1 to 6 carbon atoms, an amino group, an amide group optionally having a protecting group or a substituent, a halogen atom, or a hydrogen atom; $R_2$ independently represents an alkyl group containing 1 to 6 carbon atoms, a halogen atom, or a hydrogen atom; $R_3$ represents an alkyl group containing 1 to 6 carbon atoms, an aryl group, or a hydrogen atom; $R_4$ represents a group containing an oxygen atom, or a hydrogen atom, wherein $R_3$ may bind to $R_4$ to form a ring.

Preferably, the present invention provides a compound represented by the following formula (1A) or (2A):

wherein R1 represents an amino group, or an amide group optionally having a protecting group or a substituent.

The present invention further provides a labeling reagent for detecting a biologically-relevant substance, which comprises the aforementioned compound of the present invention.

The reagent of the present invention is preferably used to label a nucleic acid, and is preferably used in combination with a reducing agent.

The present invention further provides a method for detecting a target nucleic acid sequence, which comprises: a step of hybridizing to a target nucleic acid sequence, a first nucleic acid probe having a nucleic acid sequence complementary to a region of a portion of the target nucleic acid sequence, which is labeled with a nonfluorescent molecule having a skeleton selected from among a rhodamine skeleton, a coumarin skeleton, an ethidium bromide-derived skeleton, acridine skeleton and a dansyl skeleton and having an azido group in the molecule, and a second nucleic acid probe having a nucleic acid sequence complementary to a region of another portion of the target nucleic acid sequence, which is labeled with a molecule having reduction action; and a step of detecting a fluorescence produced by reducing the azido group of the nonfluorescent molecule in the first nucleic acid probe to an amino group.

Preferably, a nonfluorescent molecule having a rhodamine skeleton and also having an azido group in the molecule is used as said nonfluorescent molecule.

Preferably, the aforementioned compound of the present invention is used as said nonfluorescent molecule.

Preferably, the target nucleic acid sequence is RNA.

Preferably, single nucleotide polymorphism of the target nucleic acid sequence is detected.

The present invention further provides a method for analyzing a biomolecule, which comprises labeling a biomolecule with the aforementioned compound of the present invention, and detecting a fluorescence produced by reducing an azido group to an amino group by applying light to the compound.

Preferably, a biomolecule existing in a cell is labeled with the aforementioned compound of the present invention.

Preferably, a biomolecule existing in a cell is labeled with the aforementioned compound of the present invention, and a fluorescence produced by reducing an azido group to an amino group by applying light to the compound is detected by flow cytometry.

EFFECT OF THE INVENTION

The present invention provides a fluorescence-producing molecule system using the reduction reaction of an azido group as a trigger. Moreover, the present invention provides a labeling reagent for detecting a biologically-relevant substance by applying the fluorescence-producing molecule system. The labeling reagent of the present invention binds to a target DNA or RNA molecule, so that it is reduced, and thereby it produces fluorescence. The compound of the present invention has a high signal/background ratio. Thus, it enables highly sensitive gene detection and gene detection imaging in cells or organisms. Furthermore, it is not necessary to use other reagents or enzymes in the present invention, and this results in simplicity and low costs. It becomes possible to detect a gene, not only in a test tube, but also in a cell or in an organism.

BEST MODE FOR CARRYING OUT THE INVENTION

The embodiments of the present invention will be described in detail.

Figure 1:
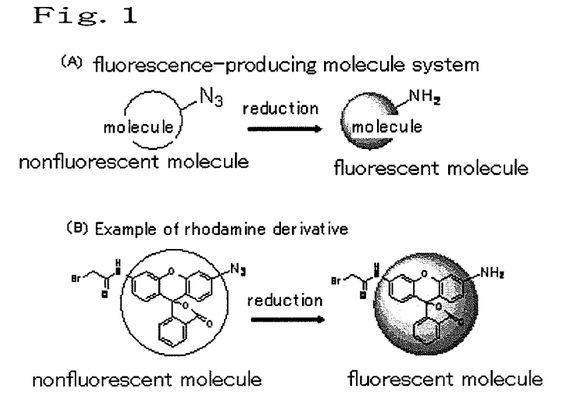
FIG. 1 shows the on-off type fluorescence sensor system of the present invention, which produces a fluorescence as a result of the structural change of a nonfluorescent molecule triggered by reduction of an azido group.
Figure 2:
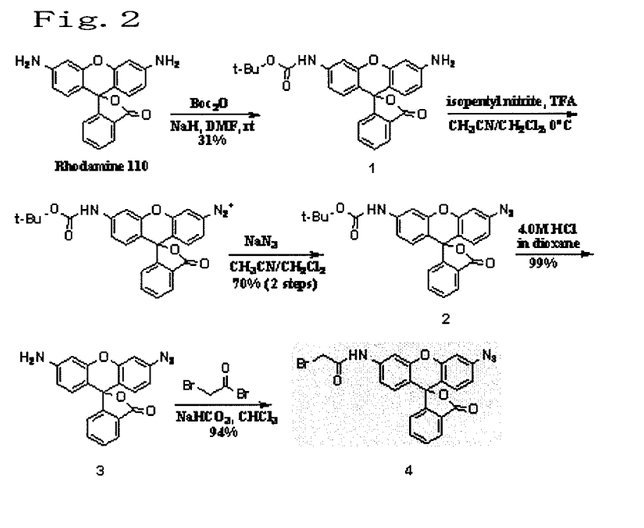
FIG. 2 shows a reaction scheme of the organic synthesis of a rhodamine azido derivative performed in the examples.

The fluorescence-producing molecule system developed by the present invention can be generalized to an on-off type fluorescence sensor system which produces a fluorescence as a result of the structural change of a nonfluorescent molecule triggered by reduction of an azido group (FIG. 1). In the examples of the present invention, a fluorescent molecule rhodamine was chemically modified, so as to synthesize a molecule into which an azido group had been introduced (FIG. 2). Rhodamine 110 was converted to mono-BOC rhodamine. Subsequently, it was treated with isoamyl nitrite to diazotize an amino group, and sodium azide was then added thereto to obtain an azide. The azide was further treated with a 4 M hydrochloric acid-dioxane solution to eliminate the BOC group. Finally, the amino group was bromoacetylated, so as to obtain an azido derivative of rhodamine (Compound 4 of FIG. 2) as a product of interest.

Figure 3:
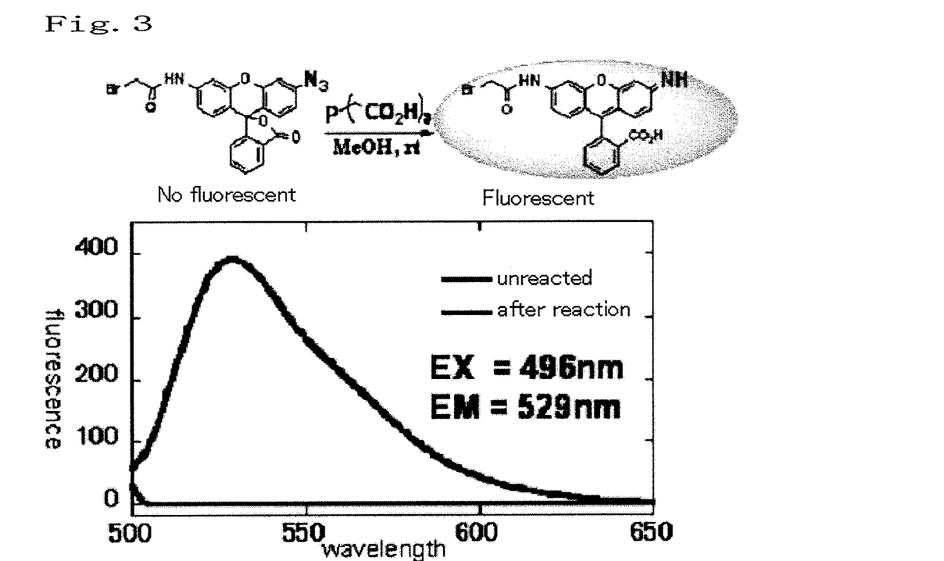
FIG. 3 shows the fluorescence of the rhodamine azido derivative of the present invention before reduction (unreacted) and that after reduction (after reaction).

The fluorescence property of this azido derivative of rhodamine (Compound 4 of FIG. 2) was analyzed. The azido derivative (Compound 4 of FIG. 2) was a nonfluorescent compound. Subsequently, Compound 4 was treated with TCEP (a phosphorus compound) (tris[2-carboxyethyl]phosphine) in methanol. As a result, the azido group was converted to an amino group, and the compound exhibited a high fluorescence property. When compared with the compound before the treatment, fluorescence intensity was increased by approximately 2,000 times (FIG. 3). The present fluorescence-producing molecule system is useful for detection of an organic phosphorus compound.

Figure 4:
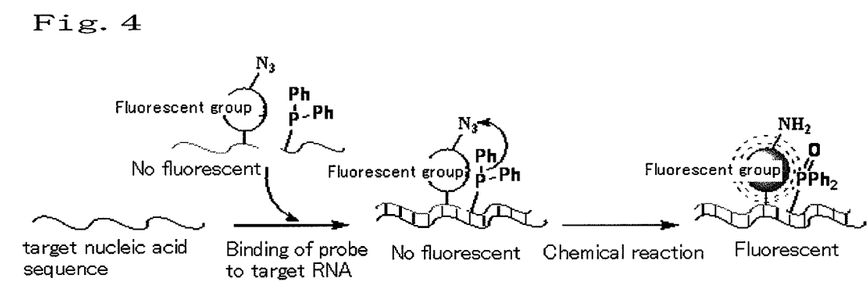
FIG. 4 shows a principle of a method for detecting a target nucleic acid sequence using the fluorescence-producing molecule of the present invention.

Further, the synthesized rhodamine derivative (Compound 4 of FIG. 2) that was the fluorescence-producing molecule system was introduced into a nucleic acid chain to develop a chemical reaction probe used in gene detection. The two DNA probes developed by the present invention (namely, the first nucleic acid probe and the second nucleic acid probe) target-sequence-specifically bind to target DNA or RNA, and they were then subjected to a chemical reaction (a reduction reaction), so that a fluorescence with high intensity can be produced (FIG. 4).

Figure 5:
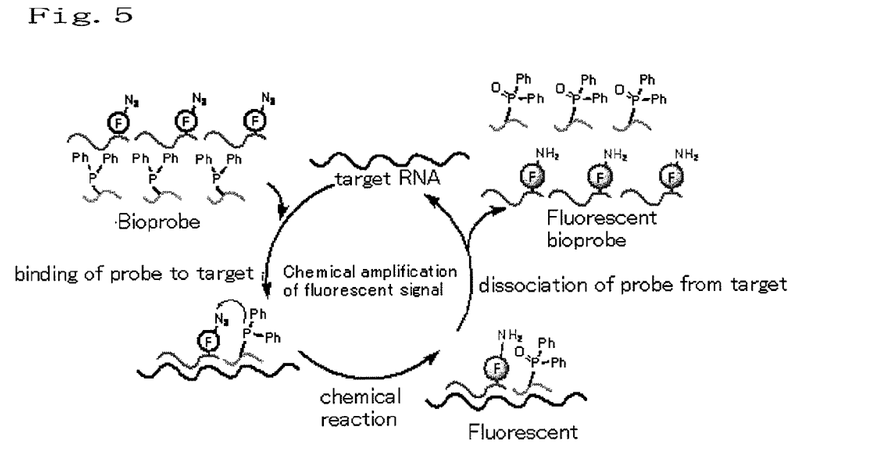
FIG. 5 shows a principle of chemical amplification of a fluorescence signal in the method for detecting a target nucleic acid sequence using the fluorescence-producing molecule of the present invention.

Using the presence or absence of this fluorescence signal or the intensity thereof as an indicator, a nucleic acid sequence can be distinguished or detected. The present reaction does not need other reagents or enzymes, and it enables measurement only by adding probes to a detection sample. Further, in the present detection reaction, a reaction cycle is rotated under isothermal conditions, and a fluorescence signal can be amplified (FIG. 5). Thus, it becomes possible to measure a trace amount of sample. Using the present probes, it becomes possible to observe gene expression even in cells or in organisms.

Figure 6:
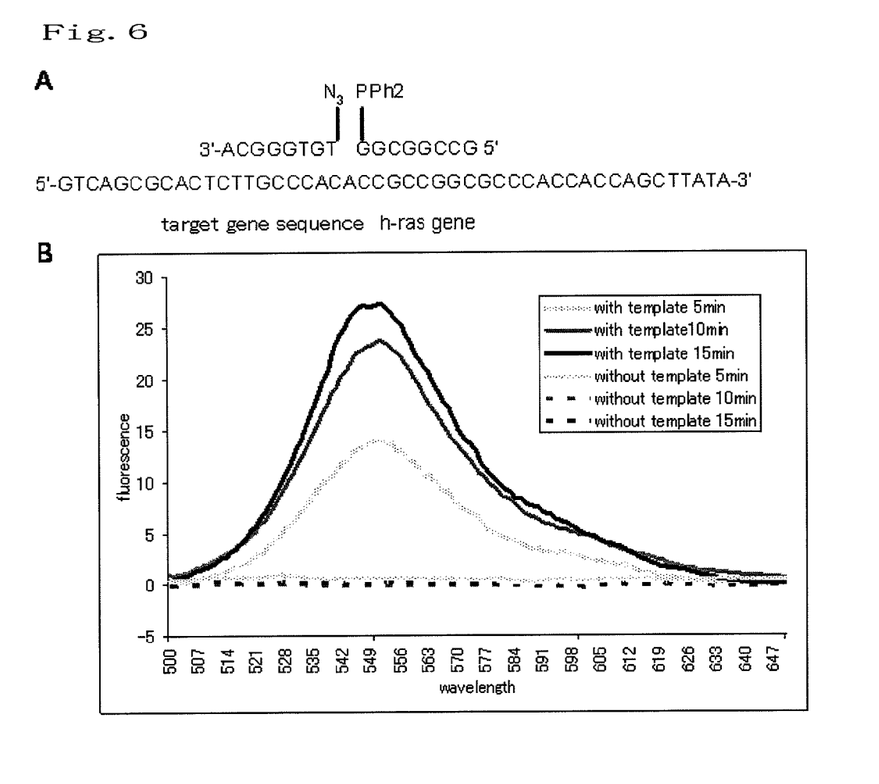
FIG. 6 shows the results obtained by fluorescent detection of a target nucleic acid sequence (SEQ ID NO: 1) using the fluorescence-producing molecule of the present invention in the examples.

Still further, in the examples of the present specification, using the probes of the present invention, an experiment was carried out to detect a human ras gene sequence. A target DNA sequence and the synthesized probes are shown in FIG. 6. In order to confirm target sequence-specific signal generation, a change in a fluorescence signal over time was measured even in the absence of the target sequence, and both results were then compared with each other. As a result, in the case of the chemical reaction probe, the fluorescence signal was significantly increased in the presence of the target sequence. On the other hand, such an increase in the fluorescence signal was not observed at all in the absence of the target sequence. Thus, it was revealed that the present chemical reaction probe generates a fluorescence signal in a target sequence-specific manner (FIG. 6).

The compound (a fluorescence-producing molecule) of the present invention is a compound represented by the following formula (1) or (2):

(1)

(2)

wherein $R_1$ represents an alkyl group containing 1 to 6 carbon atoms, an amino group, an amide group optionally having a protecting group or a substituent, a halogen atom, or a hydrogen atom; $R_2$ independently represents an alkyl group containing 1 to 6 carbon atoms, a halogen atom, or a hydrogen atom; $R_3$ represents an alkyl group containing 1 to 6 carbon atoms, an aryl group, or a hydrogen atom; $R_4$ represents a group containing an oxygen atom, or a hydrogen atom, wherein $R_3$ may bind to $R_4$ to form a ring.

Preferably, the compound of the present invention is a compound represented by the following formula (1A) or (2A):

(1A)

(2A)

wherein R1 represents an amino group, or an amide group optionally having a protecting group or a substituent.

In the present invention, an alkyl group containing 1 to 6 carbon atoms may be either a linear or branched alkyl group. The alkyl groups include a methyl group, an ethyl group, a propyl group, a butyl group, a pentyl group, and a hexyl group.

In the present invention, an amide group may have a protecting group or a substituent. The protecting groups include urethane protecting groups such as a t-butoxycarbonyl group, acyl protecting groups such as a benzoyl group, alkyl protecting groups such as a trityl group, and imine protecting groups such as dimethylacetal. As the substituent, a reactive group that reacts with a nucleic acid and binds thereto is preferable. An example of the substituent is a halogen atom. It is to be noted that such a substituent may bind to an amide group via a linking group (for example, alkylene groups such as a methylene).

In the present invention, halogen atoms include a fluorine atom, a chlorine atom, a bromine atom, and an iodine atom.

In the present invention, aryl groups include a phenyl group and a naphthyl group.

In the present invention, groups containing an oxygen atom include —O— and —OCO—.

According to the present invention, a target nucleic acid sequence can be detected by hybridizing to a target nucleic acid sequence, a first nucleic acid probe having a nucleic acid sequence complementary to a region of a portion of the target nucleic acid sequence, which is labeled with a nonfluorescent molecule having a skeleton selected from among a rhodamine skeleton, a coumarin skeleton, an ethidium bromide-derived skeleton, acridine skeleton and a dansyl skeleton and having an azido group in the molecule, and a second nucleic acid probe having a nucleic acid sequence complementary to a region of another portion of the target nucleic acid sequence, which is labeled with a molecule having reduction action; and detecting a fluorescence produced by reducing the azido group of the nonfluorescent molecule in the first nucleic acid probe to an amino group.

Specific structures of a rhodamine skeleton, a coumarin skeleton, an ethidium bromide-derived skeleton, acridine skeleton and a dansyl skeleton will be shown below.

rhodamine skeleton

R$_1$ = alkyl, amide, halogen;
R$_2$ = alkyl, halogen;
R$_3$ = alkyl;
R$_4$ = functional group including oxygen rhodamine skeleton

R$_1$ = alkyl, amide, halogen;
R$_2$ = alkyl, halogen;
R$_3$ = alkyl;
R$_4$ = functional group including oxygen coumarin skeleton

R$_2$ = alkyl, halogen

-continued
ethidium bromide-derived skeleton

R$_1$ = alkyl, amide, halogen;
R$_2$ = alkyl, halogen;
R$_3$ = alkyl acridine skeleton R$_2$ = alkyl, halogen dansyl skeleton R$_2$ = alkyl, halogen;
R$_4$ = alkyl, alchol, amine The first nucleic acid probe used in the present invention is labeled with a nonfluorescent molecule having the aforementioned skeleton and having an azido group in the molecule.

The second nucleic acid probe used in the present invention is labeled with a molecule having reduction action. The molecules having reduction action that can be used in the present invention include a sulfur compound and a trivalent phosphorus compound. An example of the sulfur compound is DTT (dithiothreitol). Examples of the trivalent phosphorus compound include triphenylphosphine and alkylphosphine.

In the present invention, the first nucleic acid probe has a nucleic acid sequence complementary to a region of a portion of the target nucleic acid sequence, and the second nucleic acid probe has a nucleic acid sequence complementary to a region of another portion of the target nucleic acid sequence. Herein, the region of the target nucleic acid sequence recognized by each of the first nucleic acid probe and the second nucleic acid probe can be arbitrarily determined, as long as it satisfies conditions in which, when the both of the above probes hybridize to the target nucleic acid sequence, the azido group of the nonfluorescent molecule in the first nucleic acid probe is reduced to an amino group by the action of the molecule having reduction action in the second nucleic acid probe. In order to satisfy the aforementioned conditions, in general, the regions of the target nucleic acid sequence recognized by the first nucleic acid probe and the second nucleic acid probe are preferably adjacent to or close to each other. The regions of the target nucleic acid sequence recognized by the first nucleic acid probe and the second nucleic acid probe are preferably close to each other across a space consisting of approximately 1 to 10 nucleotides.

When light (for example, ultraviolet light of approximately 350 nm) is applied to a fluorescence-producing molecule represented by the formula (1) or (2) or the formula (1A) or (2A), azide is reduced to amine, and a fluorescence is thereby produced. That is to say, the compound represented by the formula (1) or (2) or the formula (1A) or (2A) produces no fluorescence before irradiation of the light. After irradiation of the light, however, the compound produces a fluorescence observed at an excitation wavelength of 490 nm. That is, a biomolecule is labeled with the aforementioned fluorescence-producing molecule, and light is then specifically applied to the biomolecule. As a result, the fluorescence-producing molecule is activated, thereby enabling molecular labeling with light. This phenomenon can be used for experiments regarding single-molecule imaging or the like.

The present invention will be more specifically described in the following examples. However, these examples are not intended to limit the scope of the present invention.

EXAMPLES

Example 1

Organic Synthesis of Azido Derivative (4) of Rhodamine (1) Synthesis of Azido-Rh110-t-Boc (Compound 2 of FIG. 2)

Mono-BOC rhodamine (Compound 1 of FIG. 2) (48.0 mg, 0.112 mmol) was dissolved in acetonitrile (8 mL) and methylene chloride (4 mL) in an argon atmosphere. Thereafter, trifluoroacetic acid (12.4 µl, 0.167 mmol) and isoamyl nitrite (17.8 µl, 0.134 mmol) were further added to the solution at a temperature of 0° C., and the obtained solution was then stirred. After completion of the stirring at 0° C. for 40 minutes, sodium azide (15.0 mg, 0.223 mmol) was added to the reaction solution, and the obtained mixture was then stirred at room temperature for 30 minutes. Thereafter, a saturated sodium bicarbonate solution was added to the reaction solution, so as to terminate the reaction. Then, ethyl acetate was added thereto. An organic layer was dried over anhydrous sodium sulfate. The solvents were distilled away under reduced pressure, and the residue was then purified by flash silica gel column chromatography to obtain azido-Rh110-t-Boc (Compound 2 of FIG. 2) (36.5 mg, 80.0 µmol, 71%) in the form of a yellow crystal.

$^1$H NMR (400 MHz, CDCl$_3$) δ 1.53 (9H, s), 6.61 (1H, brs), 6.68 (1H, d, J=3.2 Hz), 6.71 (1H, d, J=3.2 Hz), 6.77 (1H, d, J=8.5 Hz), 6.87 (1H, dd, J=2.2 Hz, 8.8 Hz), 6.93 (1H, d, J=1.9 Hz), 7.12 (1H, brd, J=7.3 Hz), 7.56 (1H, brs), 7.62 (1H, dt, J=1.0 Hz, 7.5 Hz), 7.66 (1H, dt, J=1.2 Hz, 7.6 Hz), 8.02 (1H, brd, J=7.3 Hz) $^{13}$C NMR (400 MHz, CDCl$_3$) δ 28.36, 81.25, 82.19, 105.97, 107.21, 112.87, 114.26, 114.74, 115.59, 123.70, 125.07, 126.22, 128.45, 129.43, 129.78, 135.04, 140.56, 142.37, 151.47, 152.08, 152.95, 169.13 QSTAR (Applied Biosystems/MDS SCIEX) (ESI): [MH$^+$] C25H21N4O5: 457.1512, found: 457.1509

(2) Synthesis of Azido-Rh110 (Compound 3 of FIG. 2)

Azido-Rh110-t-Boc (Compound 2 of FIG. 2) (30.8 mg, 67.5 µmol) was dissolved in a 4 M dioxane hydrochloride solution (3 mL), and the obtained solution was then stirred at room temperature for 2.5 hours. Thereafter, the solvent was distilled away, and the residue was then purified using a TLC plate to obtain Azido-Rh110 (Compound 3 of FIG. 2) (23.8 mg, 66.8 µmol, 99%) in the form of a light pink solid.

$^1$H NMR (400 MHz, CDCl$_3$) δ 3.92 (2H, s), 6.36 (1H, dd, J=2.4 Hz, 8.5 Hz), 6.52 (1H, d, J=2.2 Hz), 6.55 (1H, d, J=8.5 Hz), 6.67 (1H, dd, J=2.2 Hz, 8.5 Hz), 6.74 (1H, d, J=8.5 Hz), 6.92 (1H, d, J=2.2 Hz), 7.16 (1H, d, J=7.6 Hz), 7.61 (1H, dt, J=1.0 Hz, 7.3 Hz), 7.66 (1H, dt, J=1.2 Hz, 7.5 Hz), 8.01 (1H, d, J=7.6 Hz) $^{13}$C NMR (400 MHz, CDCl$_3$) δ 82.82, 101.15, 106.95, 108.15, 111.67, 114.39, 115.82, 123.63, 124.80, 126.54, 128.93, 129.38, 129.48, 134.73, 142.03, 148.62, 151.97, 152.11, 152.73, 169.06 QSTAR (Applied Biosystems/MDS SCIEX) (ESI): [MH$^+$] C20H13N4O3: 357.0988, found: 357.0988

(3) Synthesis of Bromoacetylamido-Rh110-azido (Compound 4 of FIG. 2)

Azido-Rh110 (Compound 3 of FIG. 2) (17.9 mg, 50.2 µmol) was dissolved in chloroform (4 mL), and anhydrous potassium carbonate (138.2 mg, 1.0 mmol) was then added thereto. Bromoacetyl bromide (43.7 µl, 0.50 mmol) was slowly added to the reaction solution under cooling on ice, and the reaction solution was then stirred at room temperature for 2 hours. Thereafter, a saturated sodium bicarbonate solution was added to the reaction solution to terminate the reaction. A water layer was extracted with chloroform 2 times, and an organic layer was dried over anhydrous sodium sulfate. The reaction solution was concentrated, and the residue was then purified by silica gel chromatography to obtain bromoacetylamido-Rh110-azido (Compound 4 of FIG. 2) (22.6 mg, 47.4 mmol, 94%) as a product of interest in the form of a light yellow solid.

$^1$H NMR (400 MHz, CDCl$_3$) δ 4.03 (2H, s), 6.71 (1H, dd, J=2.2 Hz, 8.6 Hz), 6.75 (1H, d, J=8.5 Hz), 6.79 (1H, d, J=8.6 Hz), 6.95 (1H, d, J=2.2 Hz), 7.05 (1H, dd, J=2.2 Hz, 8.8 Hz), 7.13 (1H, brd, J=7.6 Hz), 7.64 (1H, dt, J=1.0 Hz, 7.6 Hz), 7.68 (1H, dt, J=1.2 Hz, 7.6 Hz), 7.74 (1H, d, J=1.9 Hz), 8.04 (1H, brd, J=6.8 Hz), 8.33 (1H, brs $^{13}$C NMR (400 MHz, CDCl$_3$) δ 29.21, 81.89, 107.11, 107.82, 114.86, 115.15, 115.43, 123.57, 125.03, 125.87, 128.38, 129.26, 129.82, 135.12, 138.86, 142.46, 151.09, 151.77, 152.68, 163.60, 169.11 QSTAR (Applied Biosystems/MDS SCIEX) (ESI): [MH$^+$] C22H14BrN4O4: 477.0198, found: 477.0196

Example 2

Change in Fluorescence Property of Azido Derivative

The azido derivative synthesized in Example 1 (Compound 4 of FIG. 2) was a nonfluorescent compound. Subsequently, this compound (Compound 4 of FIG. 2) was treated with TCEP (a phosphorus compound) (tris[2-carboxy-ethyl]phosphine) used as a reducing agent in a methanol solution. As a result, the azido group was converted to an amino group, and a high fluorescence property was exhibited. When compared with the compound before the treatment, fluorescence intensity was increased by a factor of approximately 2,000 (FIG. 3).

Example 3

Synthesis of Oligonucleotides

All oligonucleotides were synthesized according to a common phosphoroamidite method employing a DNA automatic synthesizer (H-8-SE; Gene World) using a 0.2 μM scale column. Deprotection of nucleotides and cleavage from a CPG carrier were carried out by incubation in an ammonia water at 55° C. for 4 hours. Oligonucleotides were purified using a reverse phase column (MicroPure II; Biosearch Technologies). The concentration was determined by measuring UV absorbance.

(1) Synthesis of 5' Triphenylphosphine-Linked DNA

A triphenylphosphine group was added by allowing it to react with 5' amino-modified oligo. The 5' amino-modified oligo was synthesized using 5' amino-modifier 5 (Glen Research). The reaction was carried out by intensively stirring at room temperature for 3 hours a mixed solution containing 8 mM triphenylphosphine NHS ester (in DMF), 50 mM sodium tetraborate buffer and 200 μM 5' amino-modified oligo solution (the DMF concentration in the reaction solution: 46%). The reaction product was recovered by ethanol precipitation, and it was then purified by reverse phase HPLC (gradient conditions: 0%-50% acetonitrile/50 mM triethylammonium acetate). In addition, it was confirmed by ESI-TOF mass spectrometry that a product of interest could be obtained.

5'-TGTGGGCA$^{triphenylphosphine}$-3': calculated mass, C$_{104}$H$_{126}$N$_{33}$O$_{51}$P$_9$ 2931.6; found 2932.6.

(2) Synthesis of 3' Bromoacetylamido-Rh110-Azido-Linked DNA

Bromoacetylamido-Rh110-azido (4) was added by allowing it to react with 3' phosphorothioate oligo. The 3' phosphorothioate oligo was synthesized by coupling an initial monomer with 3'-phosphate CPG and then phosphorothioating it using a sulfurizing reagent (Glen research). The reaction was carried out by intensively stirring at room temperature for 5 hours a mixed solution containing 3 mM Bromoacetylamido-Rh110-azido (in DMF), 80 mM triethylammonium bicarbonate buffer and 300 μM 3' phosphorothioate oligo solution (the DMF concentration in the reaction solution: 80%). The reaction product was recovered by ethanol precipitation, and it was then purified by reverse phase HPLC (gradient conditions: 0%-80% acetonitrile/50 mM triethylammonium acetate). In addition, it was confirmed by ESI-TOF mass spectrometry that a product of interest could be obtained.

5'-GCCGGCGG$^{Rh110-azide}$-3': calculated mass, C$_{104}$H$_{126}$N$_{33}$O$_{51}$P$_9$ 2942.5; found 2942.5.

Example 4

Reaction on DNA Template and Fluorescence Measurement

A reaction on a DNA template was carried out by reacting 500 nM each of DNA template, 5' Triphenylphosphine-linked probe and 3' Bromoacetylamido-Rh110-azido-linked probe in a ligation buffer (70 mM Tris-base, 70 mM boric acid, 10 mM MgCl$_2$ 6H$_2$O; pH 8.0) at 25° C. The following sequences were used.

DNA template: 5'-GTC AGC GCA CTC TTG CCC ACA CCG CCG GCG CCC ACC ACC AGCTTA TA -3' (SEQ ID NO: 1)

5' Triphenylphosphine-linked probe: 5'-TGT GGG CA-3'

5' Bromoacetylamido-Rh110-azido-linked probe: 5'-GCC GGC GG -3'

Fluorescence signals were analyzed using a spectrophotofluorometer (FP-6500; JASCO). Fluorescence was measured every 1 or 5 minutes. The excitation wavelength was set at 490 nm, and the fluorescence wavelength was set at 550 nm. The measurement results of fluorescence signals are shown in FIG. 6.

Example 5

6-amino-1-naphthol (95.8 mg, 0.60 mmol) and 4-carboxyphthalic anhydride (86.8 mg, 0.45 mmol) were dissolved in trifluoromethanesulfonic acid (15 mL). The obtained solution was heated at 100° C. for 3.5 hours. Thereafter, the reaction solution was added to saturated saline solution/5% sulfuric acid aqueous solution (75 mL/5 mL), and chloroform/methanol (4:1) was further added to the solution. An organic layer was washed with a saturated saline solution, and it was then dried over $Na_2SO_4$. As unpurified products, there were obtained two positional isomers derived from carboxylic acid. Thereafter, the obtained compounds were dissolved in water (5 mL), and 12 N hydrochloric acid (1 mL) and sodium nitrite (92.5 mg, 1.34 mmol) were further added to the solution at 0° C. The obtained mixture was stirred for approximately 1 hour. Thereafter, sodium azide (104.5 mg, 1.61 mmol) was further added to the reaction solution, and the mixed solution was then stirred at room temperature for 1 hour. Thereafter, chloroform was added to the reaction solution. An organic layer was washed with a saturated saline solution, and it was then dried over $Na_2SO_4$. The solvents were distilled away, and the residue was then purified by silica gel chromatography (chloroform:methanol=7:1) to obtain a bisazido derivative (16.7 mg, 31.7 μmol; two isomers) as a product of interest in the form of a yellow crystal.

$^1$H NMR (400 MHz, $CDCl_3$) δ 6.95-7.12 (2H, m), 7.26-7.37 (2H, m), 7.40-7.53 (3H, m), 7.68-7.80 (2H, m), 8.01-8.21 (2H, m), 8.29-8.32 (1H, m), 8.72-8.80 (1H, m), 12.75 (1H, brs) QSTAR (Applied Biosystems/MDS SCIEX) (ESI): [MH$^+$] C29H14N6O5: 527.103, found: 527.117

Example 6

Figure 7:
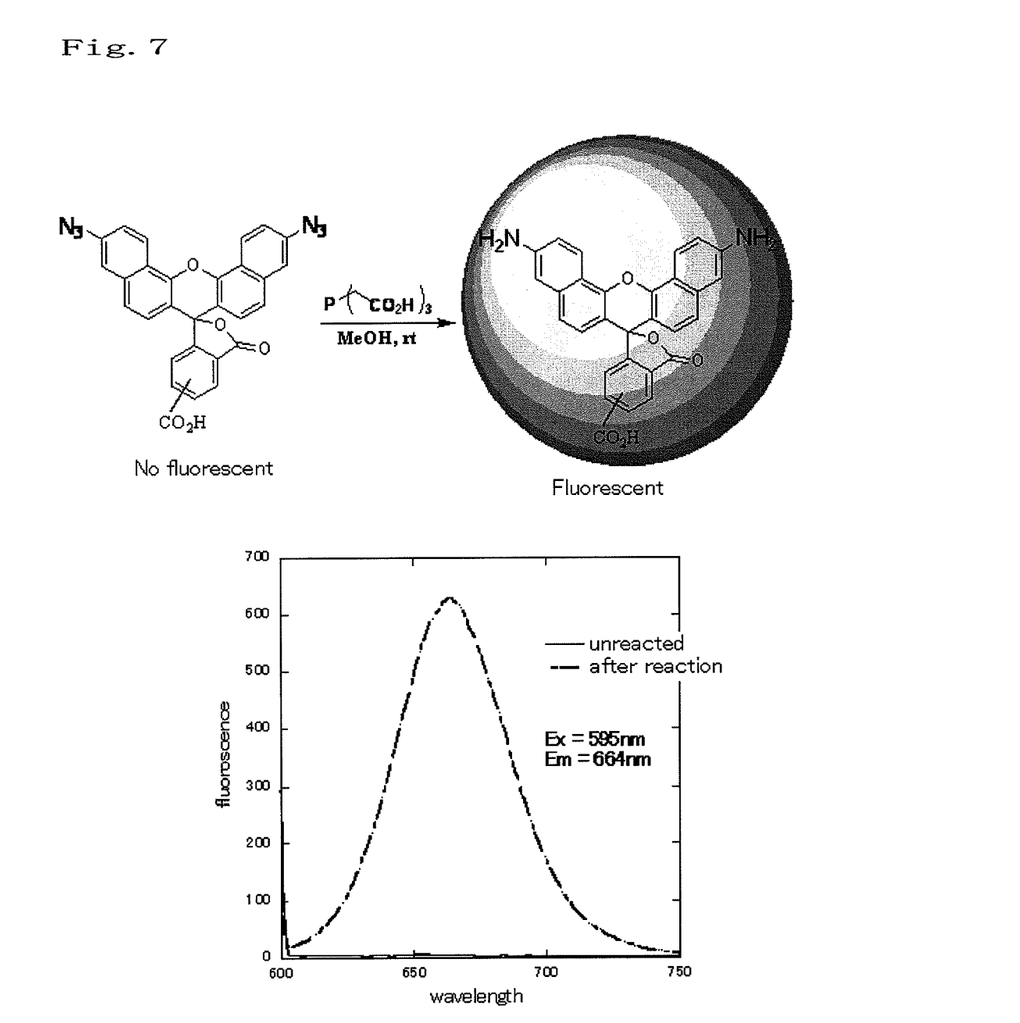
FIG. 7 shows the fluorescence of the rhodamine bisazido derivative of the present invention before reduction (unreacted) and that after reduction (after reaction).

The fluorescence property of the bisazido derivative synthesized in Example 5 was analyzed. As a result, the bisazido derivative was found to be a nonfluorescent compound. Subsequently, the bisazido derivative was treated with TCEP (a phosphorus compound) which is a reducing agent in a methanol solution. As a result, the azido group was converted to an amino group, so that the resultant compound exhibited a high fluorescence property. The fluorescence wavelength shows a maximum intensity at 664, and it was a red fluorescence. Moreover, when compared with the compound before the treatment, its fluorescence intensity was increased by a factor of approximately 1,500 (FIG. 7).

Example 7

Figure 8:
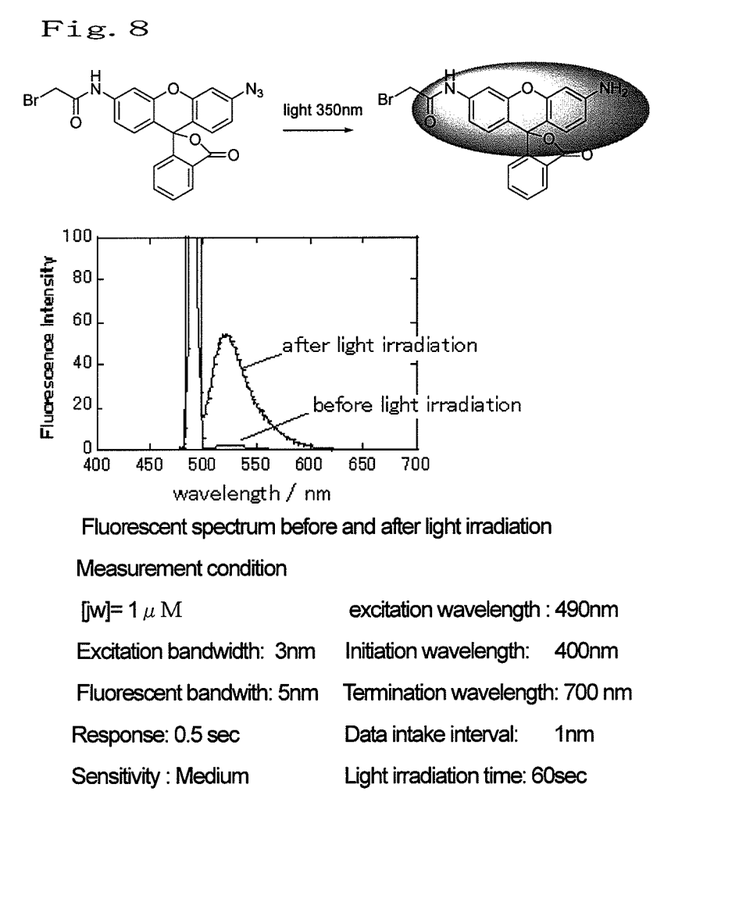
FIG. 8 shows the fluorescence of the rhodamine azido derivative of the present invention before reduction (unreacted) and that after reduction (after reaction).

The azido derivative synthesized in Example 1 (Compound 4 of FIG. 2) was a nonfluorescent compound. Subsequently, an ultraviolet light of 350 nm was applied to a methanol solution of this compound (Compound 4 of FIG. 2) (1 μM) for approximately 60 seconds. Thereafter, the fluorescence spectrum was measured using an excitation light of 490 nm (FIG. 8). The present compound does not produce fluorescence before irradiation of the light. However, after irradiation of the light, it produces a fluorescence that is observed at an excitation wavelength of 490 nm.

Example 8

SNP Detection and Reaction Using RNA as Template

Figure 9:
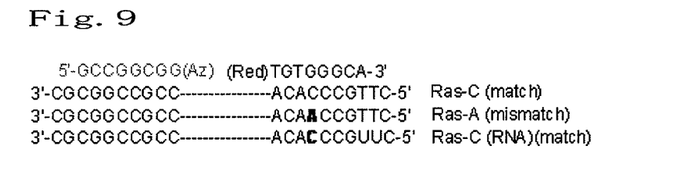
FIG. 9 shows the sequences of template and probes used in SNP detection and a reaction using RNA as a template.
Figure 10:
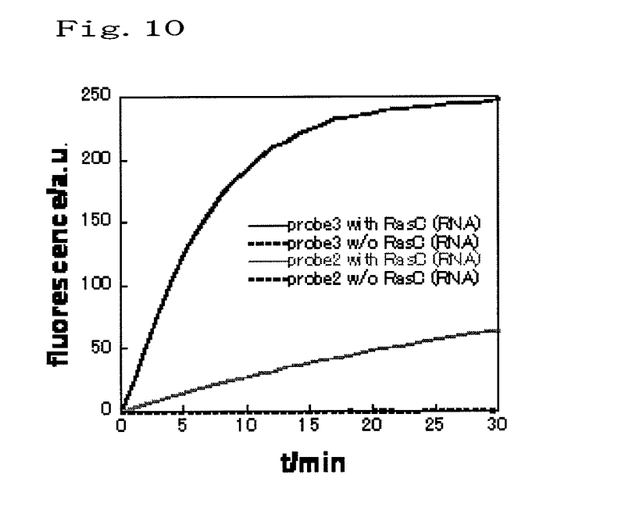
FIG. 10 shows the results obtained by performing detection using the fluorescence-producing molecule of the present invention and using RNA as a template.
Figure 11:
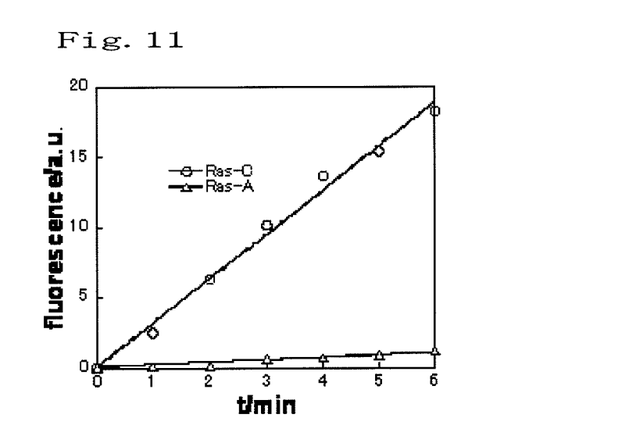
FIG. 11 shows the results obtained by identifying a single nucleotide mutation using the fluorescence-producing molecule of the present invention.

The sequences of templates and probes are shown in FIG. 9 (Az: an azido group-modified fluorescent group; Red: a reducing agent). As templates, full match DNA, single nucleotide mutation DNA, and full match RNA were prepared. Using the present probes, an experiment was carried out to detect a human ras gene sequence by the same method as that described in Example 6. As a result, as in the case of using DNA as a template, the fluorescence signal was significantly increased in the presence of a target sequence even in the case of using RNA as a template (FIG. 10). In addition, it was also possible to identify a single nucleotide mutation (FIG. 11).

Example 9

Detection of *Escherichia coli* Cells

*E. coli* K12 (NBRC 3301) was subjected to a shaking culture at 30° C. for 20 hours in Luria-Bertani Broth (NIHON SEIYAKU) sterilized with an autoclave. Thereafter, the culture solution was centrifuged at 5,000 rpm for 5 minutes, and the supernatant was then discarded. Thereafter, the cell mass was re-dispersed in a phosphate-buffered saline buffer (pH 7.2). The thus dispersed solution was fixed with 4% paraformaldehyde (Amann et al. (1990) J. Bacteriol. 172: 762-770.).

The fixed sample was immobilized on a slide glass, and 9 μL each of a hybridization buffer [0.9 M NaCl, 20 mM Tris-HCl (pH 7.2), 0.01% or 0.1% SDS, and 2.5% PEG] that contained a rhodamine azido probe (final concentration: 440 nm) and a phosphine probe (final concentration: 440 nm) was added dropwise to each well, followed by incubation at 37° C. for 30 minutes. Thereafter, the hybridization buffer was washed off with ultrapure water, and the residue was then dried. Thereafter, an antifade agent (Invitrogen Slow Fade (registered trademark) Gold antifade reagent) was placed thereon, and it was then covered with a cover glass.

The target probe was photographed with a fluorescence microscope (Carl Zeiss Axioskop (registered trademark) 2 Plus) using a high-pressure mercury lamp as a light source under conditions of ex. 480/40 and em. 510 LP. An image of the whole bacteria was observed in the form of a phase-contrast image, using a halogen lamp as a light source, and it was photographed using a black-and-white digital camera (Carl Zeiss AxioCam HRm) and software (Carl Zeiss AxioVision 3.0).

Figure 12:
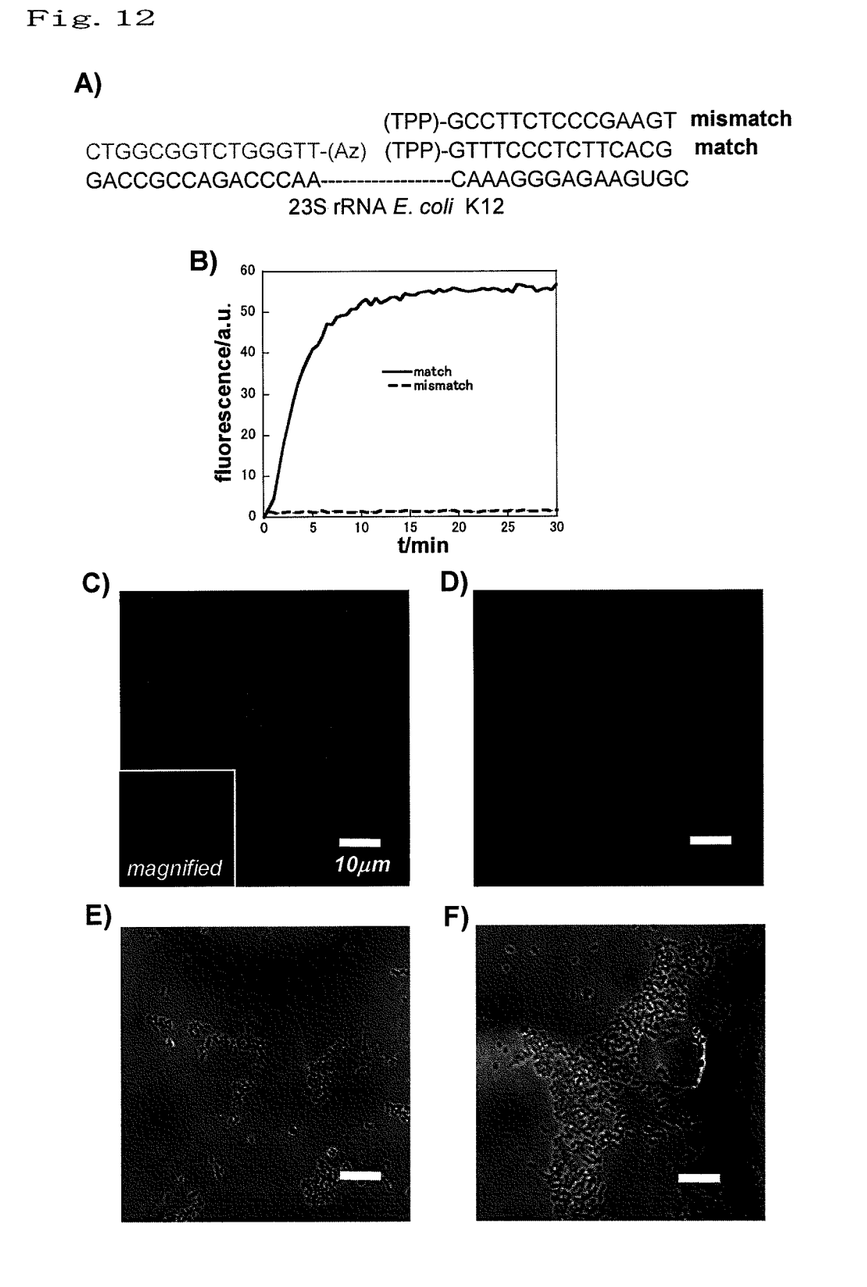
FIG. 12 shows the results obtained by detecting *Escherichia coli* cells using the fluorescence-producing molecule of the present invention.

FIG. 12A shows the sequence of *Escherichia coli* 23S rRNA used as a target and the sequences of the prepared probes. As a control, a probe with a mismatch sequence was also prepared. First, the performance of the present probes was evaluated in test tubes. As a result, a significant increase in fluorescence was observed in the probe with a full match sequence. In contrast, no such increase in fluorescence was observed in the probe with a mismatch sequence (FIG. 12B). When the present probes were actually applied to *Escherichia coli* cells, fluorescence was observed from the cells in the case of the full match probe (FIGS. 12C and 12E). On the other hand, almost no fluorescence was observed from the cells in the case of the mismatch probe (FIGS. 12D and 12F). Accordingly, it can be said that the present probes are useful also as means for detecting RNA in cells.

Figure 13:
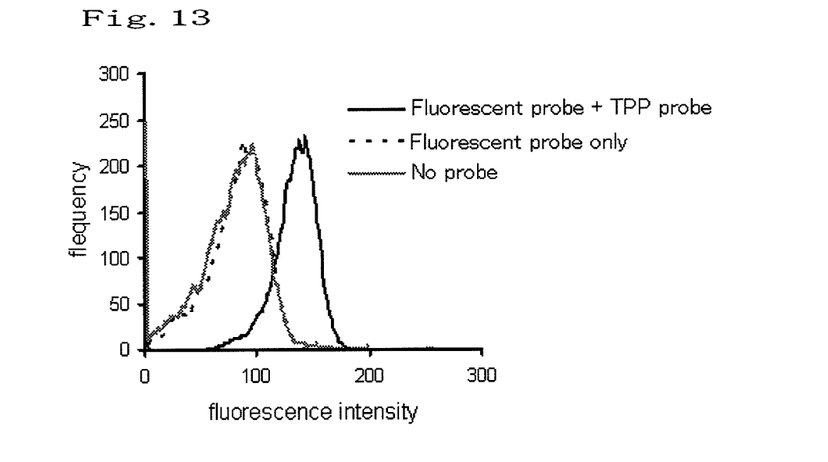
FIG. 13 shows quantification of *Escherichia coli* RNA expression by flow cytometry.

Moreover, the same *Escherichia coli* sample as described above was analyzed with a flow cytometer. FIG. 13 shows a histogram in which the horizontal axis indicates fluorescence intensity and the longitudinal axis indicates cell appearance frequency. Only in the case of introducing an RETF probe pair (a fluorescence probe and a TPP probe), there was observed a cell distribution showing a high fluorescence intensity. On the other hand, in the case of introducing only a fluorescence probe (no TPP probes), a fluorescence intensity distribution that was completely the same as in the case of only *Escherichia coli* was obtained. These results demonstrate that a fluorescence-producing molecule having an azidomethylene protecting group has no background fluorescence in cells. Thus, the results guarantee that the RETF probe has extremely high sensitivity (a high signal/background ratio).

Example 10

Imaging of 28S rRNA in Human Cells

Figure 14:
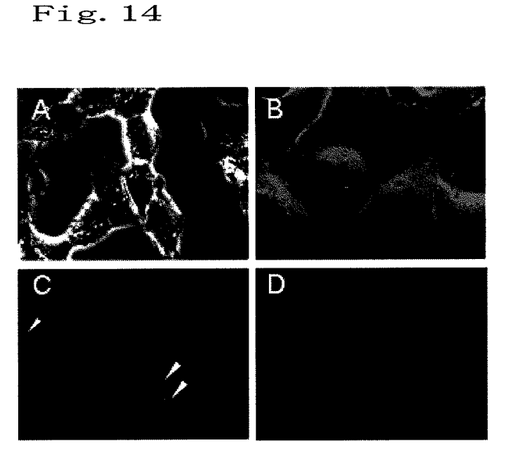
FIG. 14 shows the imaging of rRNA in human living cells using the fluorescence-producing molecule of the present invention.

Cells were cultured on a LaboTech chamber (Nunc). The cultured cells were washed with Mg, Ca-free PBS 2 times. 300 µL of a 600 nM probe (a probe that targeted 28S rRNA) and 10 U/ml Streptolysin O (SLO; Sigma-aldrich) was added to the washed cells contained in each chamber, and the obtained mixture was then incubated at room temperature for 10 minutes. In such incubation, there was used SLO, which had been sufficiently activated by incubation in 100 mM DTT for 2 hours. After completion of the incubation for 10 minutes, 300 uL of an MEM medium that contained 0.2 g/L $CaCl_2$ was added to each well, so as to inactivate the SLO. Thereafter, the cells were further incubated at 37° C. for 1 hour, and were then washed with PBS once. The detected cells were photographed using a filter with ex. 470/40 and em. 525/50 under a fluorescence microscope (Zeiss). The results are shown in FIG. 14. In FIG. 14, A indicates a rhodamine azide probe+a phosphine probe (bright field), B indicates only a rhodamine azide probe (bright field), C indicates a rhodamine azide probe+a phosphine probe (fluorescence), and D indicates only a rhodamine azide probe (fluorescence). Approximately 5 minutes after introduction of a full match probe, a fluorescence signal was observed (FIG. 14). On the other hand, no signals were observed in the case of a mismatch probe.

Industrial Applicability

When the labeling reagent of the present invention binds to a target DNA or RNA molecule and is thereby reduced, it becomes able to produce fluorescence. Since the compound of the present invention has a high signal/background ratio, it becomes possible to carry out highly sensitive gene detection as well as intracellular and in vivo gene detection imaging. Moreover, since it is not necessary to use other reagents or enzymes in the present invention, it realizes simplicity and low costs, and it becomes possible to carry out gene detection, not only in a test tube, but also in a cell or in an organism.

BRIEF DESCRIPTION OF THE DRAWINGS

FIG. 9 discloses SEQ ID NOS: 2-4, respectively, in order of appearance.

FIG. 12 discloses SEQ ID NOS 5-8, respectively, in order of appearance.

The invention claimed is:

1. A method for detecting a target nucleic acid sequence, which comprises:

hybridizing to a target nucleic acid sequence, (i) a first nucleic acid probe having a nucleic acid sequence complementary to a region of a portion of the target nucleic acid sequence, which is labeled with a nonfluorescent molecule having an azido group represented by the following formula (1A) or (2A):

wherein $R_1$ represents an amino group, or an amide group optionally having a protecting group or a substituent, wherein said nonfluorescent molecule becomes capable of emitting fluorescence when the azido group of the nonfluorescent molecule is reduced to an amino group, and (ii) a second nucleic acid probe having a nucleic acid sequence complementary to a region of another portion of the target nucleic acid sequence, which is labeled with a molecule capable of reducing the azido group of the nonfluorescent molecule in the first nucleic acid probe to an amino group, wherein said molecule capable of reducing the azido group is dithiothreitol or a trivalent phosphorus compound, and is covalently linked to the second nucleic acid probe; and detecting a fluorescence produced by reducing the azido group of the nonfluorescent molecule in the first nucleic acid probe to an amino group.

2. The method of claim 1, wherein the target nucleic acid sequence is RNA.

3. The method of claim 1, wherein a single nucleotide polymorphism of the target nucleic acid sequence is detected

* * * * *

SEQUENCE LISTING

<160> NUMBER OF SEQ ID NOS: 8

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtcagcgcac tcttgcccac accgccggcg cccaccacca gcttata      47

<210> SEQ ID NO 2
<211> LENGTH: 20
<212> TYPE: DNA
<213> ORGANISM: Homo sapiens

<400> SEQUENCE: 2
cttgcccaca ccgccggcgc      20

<210> SEQ ID NO 3
<211> LENGTH: 20
<212> TYPE: DNA
<213> ORGANISM: Homo sapiens

<400> SEQUENCE: 3
cttgccaaca ccgccggcgc      20

<210> SEQ ID NO 4
<211> LENGTH: 20
<212> TYPE: RNA
<213> ORGANISM: Homo sapiens

<400> SEQUENCE: 4
cuugcccaca ccgccggcgc      20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccttctccc gaagt      15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctggcggtct gggtt      15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic -continued

```
oligonucleotide

<400> SEQUENCE: 7
gtttccctct tcacg                                              15

<210> SEQ ID NO 8
<211> LENGTH: 30
<212> TYPE: RNA
<213> ORGANISM: Escherichia coli

<400> SEQUENCE: 8
gaccgccaga cccaacaaag ggagaagugc                              30
```